(12) United States Patent
Horn et al.

(10) Patent No.: US 7,342,659 B2
(45) Date of Patent: Mar. 11, 2008

(54) CROSS-DISPERSED SPECTROMETER IN A SPECTRAL DOMAIN OPTICAL COHERENCE TOMOGRAPHY SYSTEM

(75) Inventors: Jochen M. M. Horn, San Francisco, CA (US); Keith E. O'Hara, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 76 days.

(21) Appl. No.: 11/333,134

(22) Filed: Jan. 17, 2006

(65) Prior Publication Data

US 2006/0164639 A1 Jul. 27, 2006

Related U.S. Application Data

(63) Continuation-in-part of application No. 11/196,043, filed on Aug. 3, 2005.

(60) Provisional application No. 60/645,662, filed on Jan. 21, 2005.

(51) Int. Cl.
*G01J 3/28* (2006.01)
(52) U.S. Cl. ...................................... 356/328
(58) Field of Classification Search ......... 356/326–328
See application file for complete search history.

(56) References Cited

U.S. PATENT DOCUMENTS

| | | | |
|---|---|---|---|
| 5,565,986 A | 10/1996 | Knüttel | 356/346 |
| 5,596,407 A | 1/1997 | Zander et al. | 356/328 |
| 5,757,483 A | 5/1998 | Pierce, III | 356/305 |
| 6,362,879 B1 | 3/2002 | Ranalli | 356/328 |
| 6,487,019 B2 | 11/2002 | Hoose | 359/575 |
| 6,577,786 B1 | 6/2003 | Cappiello et al. | 385/24 |
| 6,628,383 B1 * | 9/2003 | Hilliard | 356/328 |
| 6,657,727 B1 | 12/2003 | Izatt et al. | 356/450 |
| 6,710,330 B1 | 3/2004 | Tagami et al. | 250/234 |
| 6,724,533 B2 | 4/2004 | Hoose et al. | 359/572 |
| 6,754,006 B2 | 6/2004 | Barton et al. | 359/569 |
| 6,757,113 B1 | 6/2004 | Basavanhally et al. | 359/819 |
| 6,813,019 B2 * | 11/2004 | Hammer et al. | 356/326 |
| 6,847,454 B2 | 1/2005 | Crowley et al. | 356/479 |

(Continued)

FOREIGN PATENT DOCUMENTS

JP    2000-046729    2/2000

(Continued)

OTHER PUBLICATIONS

In re U.S. Appl. No. 11/196,043, filed Aug. 3, 2005, by Jochen M. M. Horn et al., entitled Cross-Dispersed Spectrometer In A Spectral Domain Optical Coherence Tomography System.

(Continued)

*Primary Examiner*—Gregory H. Toatley, Jr.
*Assistant Examiner*—Kara E Geisel
(74) *Attorney, Agent, or Firm*—Stallman & Pollock LLP

(57) ABSTRACT

A spectral-domain optical coherence tomography system using a cross-dispersed spectrometer is disclosed. The interfered optical signal is dispersed by a grating into several orders of diffraction, and these orders of diffraction are separated by an additional dispersive optical element. The spectral interferogram is recorded by a set of linear detector arrays, or by a two-dimensional detector array.

33 Claims, 14 Drawing Sheets

U.S. PATENT DOCUMENTS

| | | | |
|---|---|---|---|
| 6,859,317 B1 | 2/2005 | Cappiello et al. | 359/569 |
| 2001/0048526 A1 | 12/2001 | Bender | 356/328 |
| 2002/0054289 A1 | 5/2002 | Thibault et al. | 356/328 |
| 2004/0239938 A1 | 12/2004 | Izatt | 356/450 |
| 2004/0239943 A1 | 12/2004 | Izatt et al. | 356/479 |
| 2005/0018201 A1 | 1/2005 | de Boer et al. | 356/479 |
| 2005/0190371 A1 | 9/2005 | Knuttel | 356/479 |
| 2005/0213103 A1 | 9/2005 | Everett et al. | 356/479 |

FOREIGN PATENT DOCUMENTS

| | | |
|---|---|---|
| JP | 2001-174404 | 6/2001 |
| WO | WO03/062802 | 7/2003 |
| WO | WO03/073041 | 9/2003 |
| WO | WO2004/043245 | 5/2004 |
| WO | WO2004/111929 | 12/2004 |

OTHER PUBLICATIONS

J. F. de Boer et al., "Improved signal-to-noise ratio in spectral-domain compared with time-domain optical coherence tomography," *Optics Letters*, vol. 28, No. 21, Nov. 1, 2003, pp. 2067-2069.

M.A. Choma, et al., "Sensitivity advantage of swept source and Fourier domain optical coherence tomography," *Optics Express*, vol. 11, No. 18, Sep. 8, 2003, pp. 2183-2189.

R. Leitgeb et al., "Performance of fourier domain vs. time domain optical coherence tomography," *Optics Express*, vol. 11, No. 8, pp. 889-894.

R.A. Leitgeb et al., "Phase-shifting algorithm to achieve high-speed long-depth-range probing by frequency-domain optical coherence tomography," *Optics Letters*, vol. 28, No. 22, Nov. 15, 2003, pp. 2201-2203.

D. Maystre et al., "Geometrical invariance property of gratings," *Applied Optics*, vol. 24, No. 2, Jan. 15, 1985, pp. 215-216.

I.S. McLean et al., "Design and Development of NIRSPEC: A Near-Infrared Echelle Spectrograph for the Keck II Telescope," *SPIE Proceedings*, vol. 3354, Mar. 1998, pp. 566-578.

E. Popov et al., "Almost perfect blazing by photonic crystal rod gratings," *Applied Optics*, vol. 40, No. 15, May 20, 2001, pp. 2417-2422.

L.M. Smith, et al., "Absolute displacement measurements using modulation of the spectrum of white light in a Michelson interferometer," *Applied Optics*, vol. 28, No. 15, Aug. 15, 1989, pp. 3339-3342.

T.H. Ko, et al., "Comparison of Ultrahigh- and Standard-Resolution Optical Coherence Tomography for Imaging Macular Pathology," *Ophthalmology*, vol. 112, No. 11, Nov. 2005, pp. 1922.e1-1922.e15.

M. Wojtkowski et al., "Real-time in vivo imaging by high-speed spectral optical coherence tomography," *Optics Letters*, vol. 28, No. 19, Oct. 1, 2003, pp. 1745-1747.

I. Zeylikovich et al., "Nonmechanical grating-generated scanning coherence microscopy," *Optics Letters*, vol. 23, No. 23, Dec. 1, 1998, pp. 1797-1799.

Book by Christopher Palmer, *Diffraction Grating Handbook, 5th edition*, published by Thermo RGL, Richardson Grating Laboratory, (Rochester, New York), Copyright 2002, printed from http://www.gratinglab.com/library/handbook5/handbook.asp., 204 pages in length.

* cited by examiner 401   402   Fig. 4   403

Top view

Locations of the spectral range 785nm–915nm
in diffraction order $m=36$ through order $m=44$;
with markers placed every 5nm.

CROSS-DISPERSED SPECTROMETER IN A SPECTRAL DOMAIN OPTICAL COHERENCE TOMOGRAPHY SYSTEM

PRIORITY

This application is a continuation-in-part of U.S. patent application Ser. No. 11/196,043, filed on Aug. 3, 2005.

This application claims the benefit of the filing date under 35 U.S.C. § 119(e) of U.S. Provisional Patent Application Ser. No. 60/645,662, filed Jan. 21, 2005.

BACKGROUND OF THE INVENTION

1. Field of the Invention

The invention relates generally to optical coherence tomography, specifically to the use of a cross-dispersed, echelle configuration, spectrometer in a spectral domain optical coherence tomography system.

2. Description of Related Art

Optical Coherence Tomography (OCT) is a technology for performing high-resolution cross sectional imaging that can provide images of tissue structure on the micron scale in situ and in real time. In recent years, it has been demonstrated that spectral domain OCT has significant advantages in speed as compared to time domain OCT. In spectral domain OCT (SD-OCT) the optical path length difference between the sample and reference arm is not mechanically scanned but rather the interferometrically combined beam is sent to a spectrometer in which different wavelength components are dispersed onto different photodetectors to form a spatially oscillating interference fringe (Smith, L. M. and C. C. Dobson (1989). "Absolute displacement measurements using modulation of the spectrum of white light in a Michelson interferometer." *Applied Optics* 28(15): 3339-3342). A Fourier transform of the spatially oscillating intensity distribution can provide the information of the reflectance distribution along the depth within the sample. As there is no mechanical depth scanning, acquisition of light reflection along a full depth range within the sample can be achieved simultaneously, and consequently, the speed of obtaining a full depth reflection image is substantially increased as compared to time domain OCT (Wojtkowski, M., et al. (2003). "Real-time in vivo imaging by high-speed spectral optical coherence tomography." *Optics Letters* 28(19): 1745-1747; Leitgeb, R. A., et al. (2003). "Phase-shifting algorithm to achieve high-speed long-depth-range probing by frequency-domain optical coherence tomography." *Optics Letters* 28(22): 2201-2203). In addition, as the light reflected from the full depth range within the sample is fully dispersed over many photodetectors, the shot noise for each photodetector is substantially reduced as compared to the time domain OCT case, and hence the signal to noise ratio can also be substantially increased (Leitgeb, R. A., et al. (2003). "Performance of Fourier domain vs. time domain optical coherence tomography." *Optics Express* 11(8): 889-894; De-Boer, J. F., et al. (2003). "Improved signal-to-noise ratio in spectral-domain compared with time-domain optical coherence tomography." *Optics Letters* 28(21): 2067-2069; Choma, M. A., M. V. Sarunic, et al. (2003). "Sensitivity advantage of swept source and Fourier domain optical coherence tomography." *Optics Express* 11(18): 2183-2189).

SD-OCT systems seek to achieve high axial resolution at moderate scan depths or moderate axial resolution at large scan depth. For example, in current applications to retinal diagnosis, retinal images with approximately 2 microns resolution over a depth of approximately 2 mm are desired (Ko, T. H., J. G. Fujimoto, et al. (2005). "Comparison of Ultrahigh- and Standard-Resolution Optical Coherence Tomography for Imaging Macular Pathology." *Ophthalmology* 112(11): 1922-1935). In current applications to prescription of intraocular lenses (Hitzenberger, C. (1991). "Optical measurement of the axial eye length by laser Doppler interferometry." *Invest. Ophthalmol. Vis. Sci.* 32(3): 616-624), all optical interfaces within the eye (up to 30 mm long) need to be located with a resolution of around 30 microns. For these two applications the desired ratio of scan depth in tissue to axial resolution is about the same (30 mm/30 microns vs. 2 mm/2 microns) and higher values of the ratio give further improvements to the images. In straightforward SD-OCT techniques the information in one axial scan is encoded in the spectrum (Leitgeb, R. A., et al. *Optics Express* 11(8): 889-894). A large ratio of scan depth to axial resolution implies large information content within one axial scan, which in turn requires a large number of pixels along a linear detector array; the examples above require at least 4000 pixels. Given the typical 10-micon spatial optical resolution of a spectrometer operating at wavelengths near 1 micron (typical for biological applications) resolving the information content in the spectrum requires a spectrum length of approximately 40 mm. Such arrays are not commonly available and even if such an array would be made available, the optics layout would necessarily be very large even in a Littrow arrangement, causing thermal problems for example.

A solution to this problem would be the use of a cross-dispersed echelle spectrometer. In such a configuration, the light emerging the fiber or pinhole is collimated before it hits the echelle grating. An echelle is a coarsely ruled grating (for example of the order of 50 grooves per millimeter) that is designed to be used in high orders of diffraction, denoted by m, typically m=30 or higher in order to achieve the desired spectral resolution. In such a configuration, the spectral width of the source ($\Delta\lambda$>130 nm for high resolution OCT) is diffracted into several orders, and these orders will overlap. That is, at a given angle of diffraction, several discrete wavelengths within the bandwidth of the source will be diffracted at that angle, each wavelength being diffracted in a different order of diffraction. Thus if the dispersed spectra would fall onto a linear detector array, each detector in the array would receive several wavelengths, each wavelength from a different order of diffraction. To separate the light from these different orders of diffraction, an optical element providing relatively low dispersion can be placed after the echelle with its dispersion direction perpendicular to the echelle grating's dispersion direction. A low-dispersive element used in this way is called cross-disperser. The different diffraction orders are now spatially separated, and can now be imaged with a 2-dimensional area detector array or with a stack of linear detector arrays. Such spectrometers can be built up in the classical way; that is, collimating the light emerging the fiber before it falls onto the echelle grating, re-imaging the dispersed light with a lens system onto a two-dimensional detector array after it has been cross-dispersed.

Cross-dispersed echelle spectrographs have been used mostly in the field of astronomy, where extreme wavelength resolutions are required, for example R>100,000 and where the recent availability of 2D infrared detector arrays allows the imaging of multiple, cross-dispersed echelle orders (see e.g. McLean et al., 1998, SPIE Proceedings Vol. 3354, pp 566). There, the echelle grating is also used in a Littrow arrangement in order to save space, because it needs to be cryogenically cooled. However, these prior art echelle spectrographs are typically geared towards the highest possible spectral resolutions, whereas spectral-domain OCT typically requires resolutions in the range of 2,000<R<10,000.

This cross-dispersed spectrometer can achieve the benefits of compactness and stability of alignment described in co-pending application Ser. No. 11/196,043, filed on Aug. 3, 2005 (incorporated herein by reference) by using the echelle grating in the Littrow configuration. In order to separate the diffracted beams from the input beam, the echelle grating can be tipped to produce conical diffraction. The conical diffraction creates certain distortions and non-linearities in the focused beam. These problems are described in greater detail below with respect to FIG. 3. One aspect of the subject invention is to provide optical correction for such distortions.

SUMMARY OF THE INVENTION

The present invention discloses a design for high-resolution spectrometers in a cross-dispersed echelle or echelon configuration and the use of such spectrometers for SD-OCT systems. Such a cross-dispersed Echelle grating can also be used in a previously disclosed Littrow arrangement.

The spectrometer includes a first grating for dispersing the incoming light beam as a function of wavelength. This grating typically is a coarsely ruled echelle grating operating in high diffraction orders m>30 for example. The spectral range that needs to be covered in a high resolution SD-OCT system will therefore fall in multiple (for example five) diffraction orders, which spatially overlap. This echelle grating is followed by a second dispersive element which can be a grating or a prism, with its dispersion direction oriented perpendicular to the echelle grating thus eliminating the spatial order overlap from the light diffracted at the echelle grating. A linear detector array receives and measures the diffracted, dispersed light of interest.

The incoming beam, the echelle, and the array are preferably positioned in a substantially Littrow condition so that the diffracted beam propagates along an axis near to the incoming beam. Those skilled in the art often use the term Littrow configuration to define an arrangement wherein some of the diffracted light beams of interest propagate close to the propagation axis of the incoming beam. The specification and claims will use the term Littrow configuration (or arrangement or condition) as it is more broadly defined. As an alterative to using this term, a compact spectrometer arrangement can also be defined as a configuration where a common lens is used to focus both the incoming and diffracted beams of interest.

In one aspect of this invention, the orientation of the echelle is tilted or tipped to induce conical diffraction in order to spatially separate the incoming beam from the diffracted beams to be measured. The conical diffraction will create certain non-linearities in the footprint of the beam with respect to the planar linear array. In one aspect of the invention, optical elements are provided for reducing these non-linearities.

In another aspect of the invention, the compact spectrometer is used as the detecting element in a spectral domain optical coherence tomography system (SD-OCT). In one embodiment, the spectrometer is in a substantially Littrow configuration. Alternatively, the spectrometer includes a common lens for focusing both the incoming and diffracted beams that are measured. In either case, it is preferable, though not necessary to use conical diffraction to vertically separate the incoming and diffracted beams. In the case of conical diffraction, it is preferable, but not required, to provide for correction for distortion and/or non-linearities in the footprint of the diffracted beam.

Various other possible improvements are possible for a preferred spectrometer. For example, the spectrometer can be designed with features to reduce the sensitivity to thermal variations. In addition, the spectrometer can be designed to generate an output that is substantially insensitive to the polarization state of the incoming beam.

The primary advantage of a cross-dispersed spectrometer for SD-OCT is that it gives high dispersion on the detector array, higher dispersion meaning more pixels per nm of spectral range, without requiring the large field of view that a high-dispersion linear spectrometer would require. Stacking portions of the spectrum atop one another makes the spectrum more compact, and thus makes more compact the region over which the imaging optics must perform well. Greater dispersion increases the resolution of the spectrometer, allowing close fringes to be resolved, giving better depth range to the tomograms.

A cross-dispersed spectrometer that uses a two-dimensional detector array can easily accept additional fiber inputs from additional couplers, putting additional spectra above/below each other on the detector array. In SD-OCT these additional inputs could be used for balanced detection or phase-sensitive detection.

A cross-dispersed spectrometer can use the compact, inexpensive, area sensors that are available for consumer applications, to form the basis of a compact, low-cost OCT scanner. A cross-dispersed spectrometer can use multiple line-scan sensors for its detector array. These line-scan sensors can be read out simultaneously, allowing a faster data acquisition rate.

These and other features and advantages of the present invention will become more readily apparent to those skilled in the art upon review of the following detailed description of the preferred embodiments taken in conjunction with the accompanying drawings.

BRIEF DESCRIPTION OF THE DRAWINGS

FIG. 6 (b) shows a top view of FIG. 6 (a).

FIG. 7 (b) shows a secondary preferred embodiment of the cross-dispersed echelle spectrograph in Littrow configuration as in FIG. 7 (a), except that a field flattening lens has been inserted.

FIG. 7 (c) shows an alternative embodiment of the cross-dispersed echelle spectrograph.

FIG. 10 (b) shows that with the insertion and appropriate placement of a field flattening lens that has an approximately 3.1% positive (pincushion) distortion, the focused spectral line can be straightened to have only a maximum of 1 micron deviation from a straight line.

FIG. 11 (b) shows a hybrid metallic-dielectric grating that has a metallic base layer and layers of dielectric materials of varying refractive index to render the grating substantially polarization independent.

FIG. 11 (c) shows a lamellar volume grating that has an approximately rectangular grating profile with a height-to-width ratio of the grooves greater than two to render the grating substantially polarization independent.

FIG. 11 (d) shows a grating with a substrate and a reflective material adjacent the substrate to render the grating substantially polarization independent.

FIG. 11 (e) shows a blazed photonic crystal grating made with embedded circular rods in another optical medium that has a high diffraction efficiency and a high degree of polarization independence.

DETAILED DESCRIPTION OF THE INVENTION

As is well known to those skilled in the art, a broad band light beam can be dispersed into its spectral components in a number of ways, including the use of a prism, a grating, an arrayed waveguide grating or a combination of optical filters. A grating is generally used in most spectrometers because of its high resolving power and hence high spectral resolution within a limited space. In many applications, a plane grating is preferred because of its low cost as compared to other more complex gratings such as a curved grating, a volume holographic grating, or a photonic crystal grating.

Figure 1:
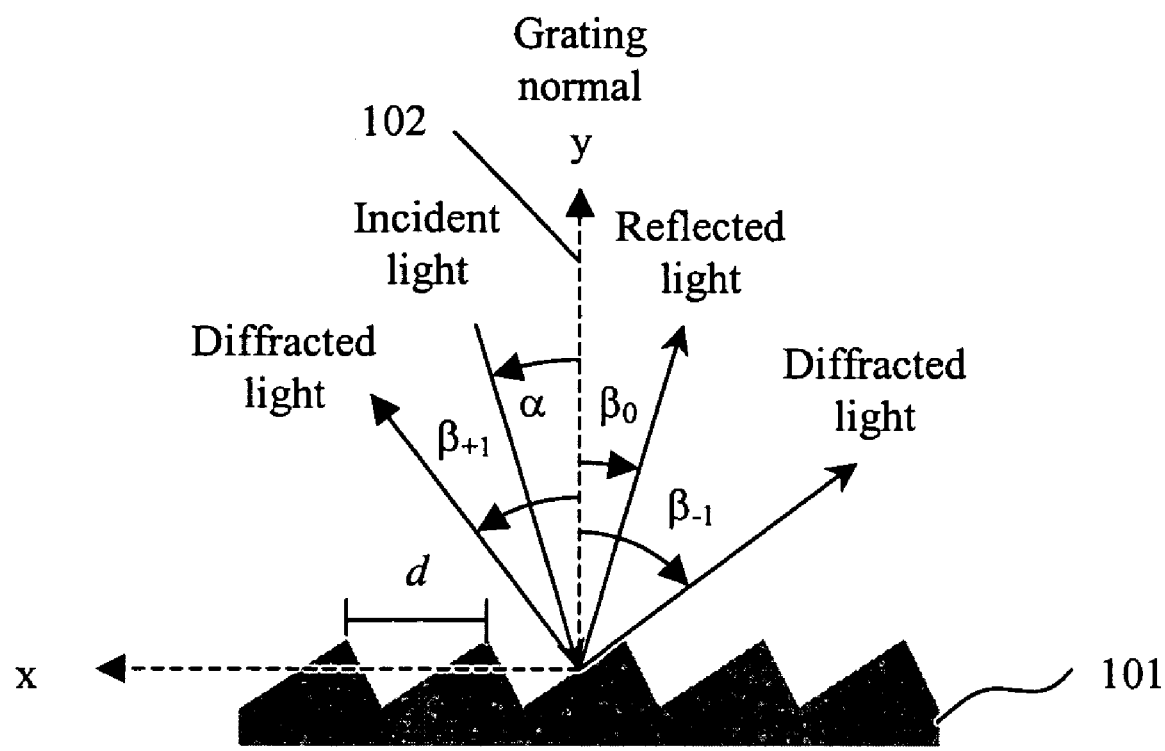
FIG. 1 shows a plane reflection grating being used in the normal classical or in-plane configuration to diffract an incident light beam into multiple diffracted orders.

FIG. 1 shows the case of a plane reflection grating 101, the grating equation is given by $$m\lambda = d(\sin \alpha + \sin \beta_m) \quad (1)$$

where m is the diffraction order which is an integer, $\lambda$ is the wavelength of light, d is the grating period, $\alpha$ is the angle of incidence, and $\beta_m$ is the angle of diffraction. The angle of incidence and angle of diffraction are measured from the grating normal 102, i.e. the dashed line perpendicular to the grating surface. The angle sign convention is that angles measured counter-clockwise from the normal are positive and angles measured clockwise from the normal are negative. We denote the x-axis in FIG. 1, the axis in the plane of the grating perpendicular to the grooves, as the dispersion axis.

For a given diffraction order m, the angular dependence of the diffracted spectral components upon the wavelength is given by $$\beta_m(\lambda) = \arcsin\{m\lambda - \sin \alpha\} \quad (2)$$

It should be pointed out that the validity of Equ. (1) is restricted to cases in which the incident and diffracted light rays are perpendicular to the grating grooves, which is called the classical or in-plane diffraction.

Figure 2:
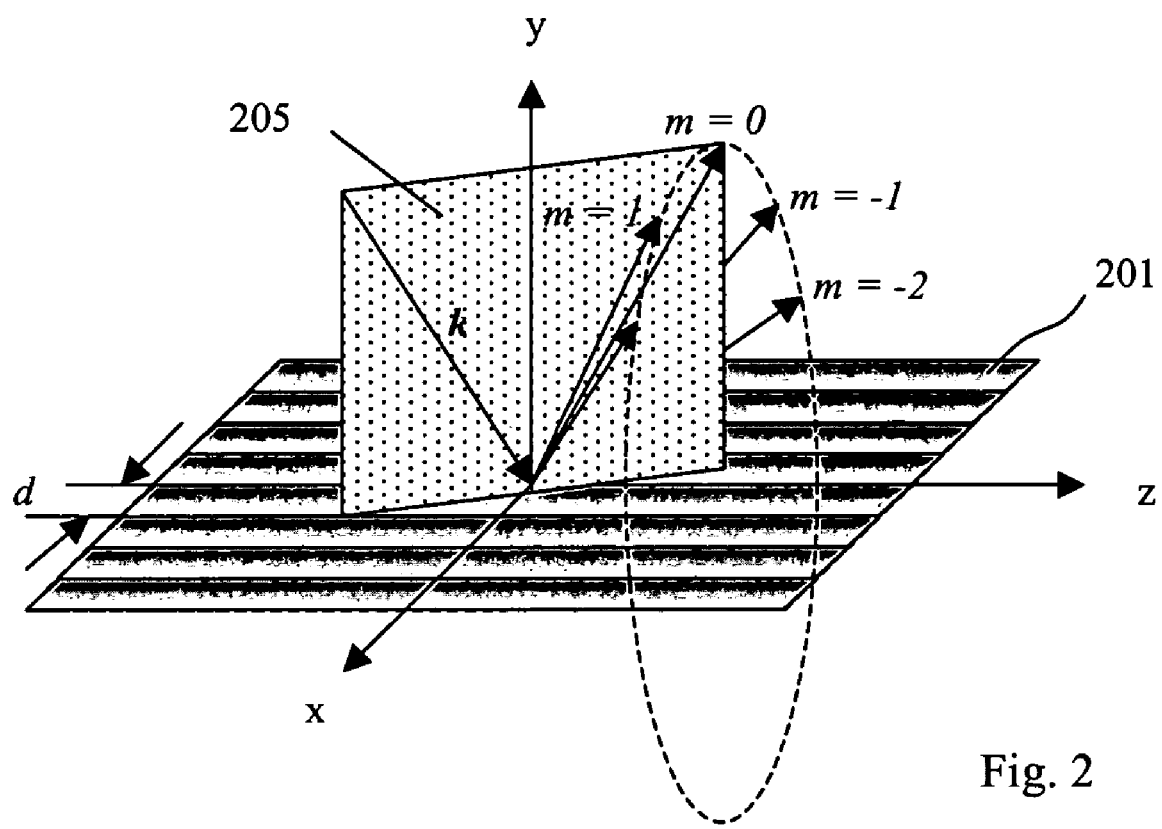
FIG. 2 shows a general case of conical diffraction where a rectangular coordinate system Oxyz is assumed with the grating groove parallel to the z-axis.

If the incident light beam is not perpendicular to the grooves, the grating equation must be modified to $$m\lambda = d \cos \epsilon (\sin \alpha + \sin \beta_m) \quad (3)$$

where $\epsilon$ is the angle between the incident light path and the plane perpendicular to the grooves. When $\epsilon \neq 0$, the diffracted spectra lie on a cone rather than a plane and the diffraction is called conical diffraction. To better understand conical diffraction, let us consider a rectangular coordinate system Oxyz with the grating groove 201 parallel to the z-axis as shown in FIG. 2. An incident plane wave, with a wave vector of $k=(k_x e_x + k_y e_y + k_z e_z)$ and its modulus $|k|=(2\pi/\lambda)$, falls on the grating at an arbitrary off-plane direction as shown by the dotted plane 205 in FIG. 2. From diffraction theory (see for example, Maystre D. et al. (1985) "Geometrical invariance property of gratings" Applied Optics 24(2): 215-216), $$k_{mx} = k_x + m\frac{2\pi}{d} \quad (4)$$

$$k_{my} = \sqrt{k^2 - k_{mx}^2 - k_{mz}^2}$$

$$k_{mz} = k_z$$

The above equation tells us that $k_m$ and k have the same modulus. As $k_{mz}=k_z$ for all the diffraction orders m, the various diffracted order wave vectors will lie on a cone formed by the origin of the coordinate system Oxyz and the dashed circle as shown in FIG. 2. The projection of all the diffracted order wave vectors onto the xy plane will result in a diagram similar to FIG. 1 with the difference that the xy plane component modulus of the various diffracted order wave vectors is the projection of k onto the xy plane, i.e. $|k_{mx}e_x + k_{my}e_y| = |k_x e_x + k_y e_y| = |k|\cos \epsilon$, where $\epsilon$ is the angle between the incident wave vector and the xy plane. Therefore, Equ. (3) instead of Equ. (1) should be used and the angles in Equ. (3) are those corresponding to the wave vectors projected onto the xy plane.

The efficiency of diffraction for a particular diffraction order m can be adjusted by changing the groove facet angles, or their shape and depth. The optimization of efficiency by appropriate groove shaping is known as blazing. In many applications, planar blazed holographic gratings and planar blazed diffraction gratings are used because of their high efficiency combined with their low cost and high resolving power.

A particularly useful case is a blazed diffraction grating operating in the Littrow configuration where the grating is set at an angle such that, for the range of wavelengths collected and the desired order of diffraction m, approximately $\alpha \approx \beta_m$; the diffracted beams nearly return on the path of the incident beam. (See for example, U.S. Pat. No. 6,710,330, U.S. Pat. No. 6,859,317).

Figure 3:
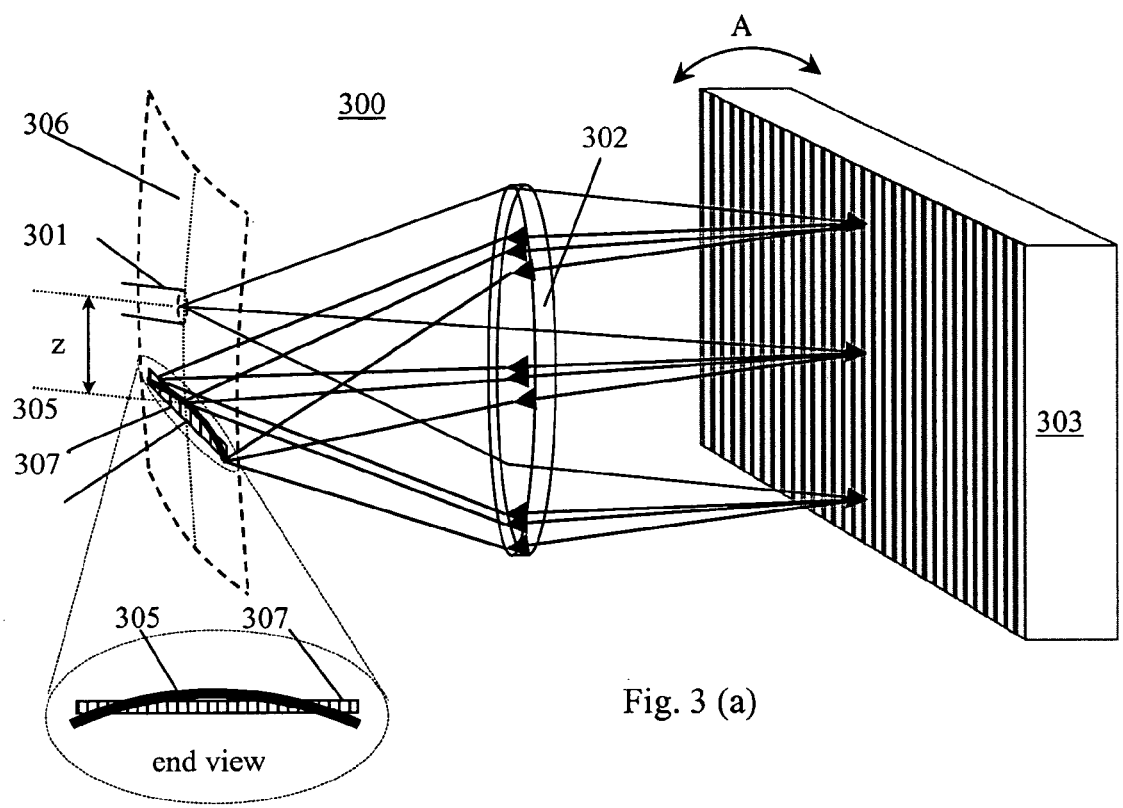
FIG. 3(a) shows a perspective view of Littrow conical diffraction, in which the light is diffracted back approximately toward the direction of incidence, and the incident and diffracted light beams are also separated from each other through conical diffraction.
FIG. 3(b) shows a top view of the configuration of FIG. 3(a).
Figure 3:
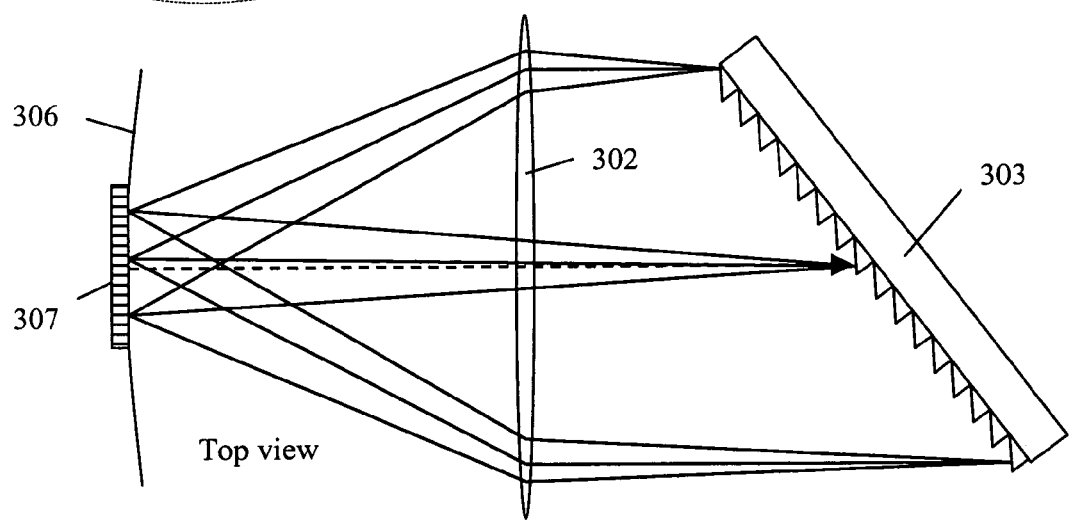

FIG. 3(a) shows a perspective view of an example of a conical diffraction Littrow configuration 300, in which light from an optical fiber 301 is collimated by a common lens 302 and propagates towards a blazed reflection grating 303. To create conical diffraction, the grating is tilted or tipped about the axis shown by arrow A. If the grating were not tipped, and oriented such that the incident light was perpendicular to the grating grooves, the diffracted light would return along the path of the incident beam so that the footprint 305 of the diffracted light would form a spectrum substantially centered on the output end of the fiber 301 (i.e. the in-plane Littrow condition). (See also the top view of FIG. 3(b)).

Tipping the grating creates conical diffraction which, as shown in FIG. 3(a), vertically displaces the footprint of the diffracted light by an amount "z" thereby permitting the light to be detected by pixel array 307.

A key issue with such an arrangement, however, is that due to the non-planar effects introduced by conical diffraction, the diffracted light beam vectors will lie on the surface of a cone and as a result, when the spectrally dispersed beams are focused by lens 302, the footprint of the focused light will be curved 305 (as can be seen from the inset end view in FIG. 3(a)). More particularly, the footprint will have a non-linearity with respect to the linear axis of the detector array such that the focused region will be higher on the z axis at the center of the array than at the opposed ends. If a standard linear detector array 307 such as that of a line scan camera is used, depending on the spectral width of the input beam, portions of the focused curved spectral line may fall outside the photosensitive area of the detector array 307. This is especially true for a high axial resolution SD-OCT system in which a broadband light source is desired. In addition, such a focused curved spectral line may also make the spectrometer output very sensitive to mechanical vibration and temperature changes that may cause portions of the focused spectral line fall off the pixels.

One possible solution is to use a curved rather than a standard linear detector array to match the shape of the curved focused spectral line. However, this would require a custom-made line scan camera and hence would mean a high cost. A second solution is to make the shape of the detector array pixels rectangular rather than square as is commonly the case for line scan cameras so that they can tolerate some movement of the focused spectral line with respect to the pixels. The larger photosensitive area of such taller rectangular pixels, however, implies greater capacitance of the photosensitive area, which makes fast readout more difficult. Most commercial high-speed line scan cameras are meant for completely different applications such as for optical document scanners, and hence the pixel height of these cameras is generally not large enough to compensate for the bending of the focused spectral line resulting from the broad bandwidth of a light source for a high axial resolution SD-OCT system.

Figure 4:
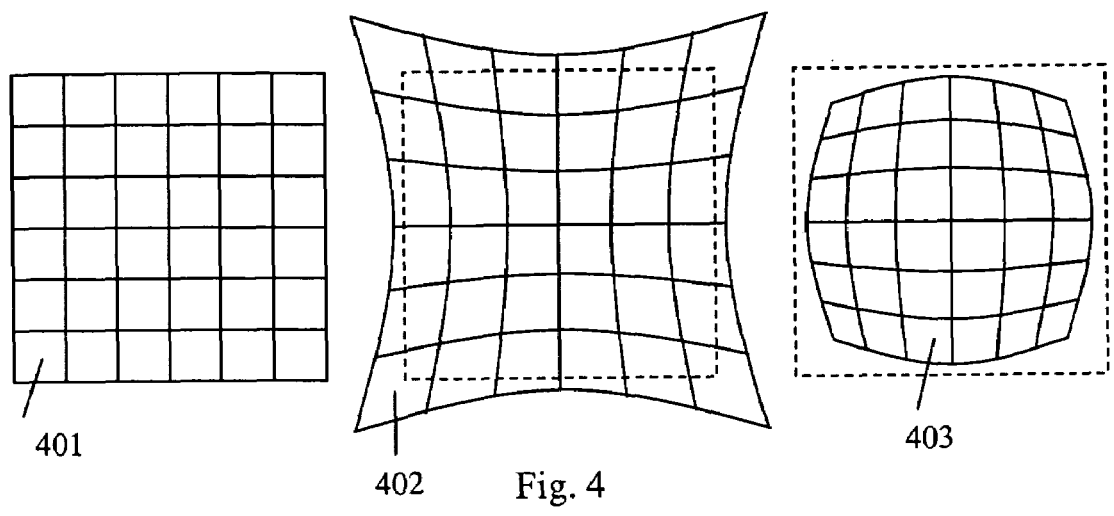
FIG. 4 shows distortion due to lens aberration, in which the left image is a perfect image without any distortion, the middle one is an image with positive (also called pincushion) distortion and the right one is an image with negative (also called barrel) distortion.

A lens is selected for reducing the non-linearity caused by the conical diffraction so that the registration of the footprint of the diffracted beam and the array is improved. As is well known to those skilled in the art, an aberrant lens can have a positive (also called pincushion) distortion or a negative (also called barrel) distortion as shown in FIG. 4, in which the left image 401 is a perfect image without any distortion, the middle one 402 is an image with positive distortion and the right one 403 is an image with negative distortion.

Figure 5:
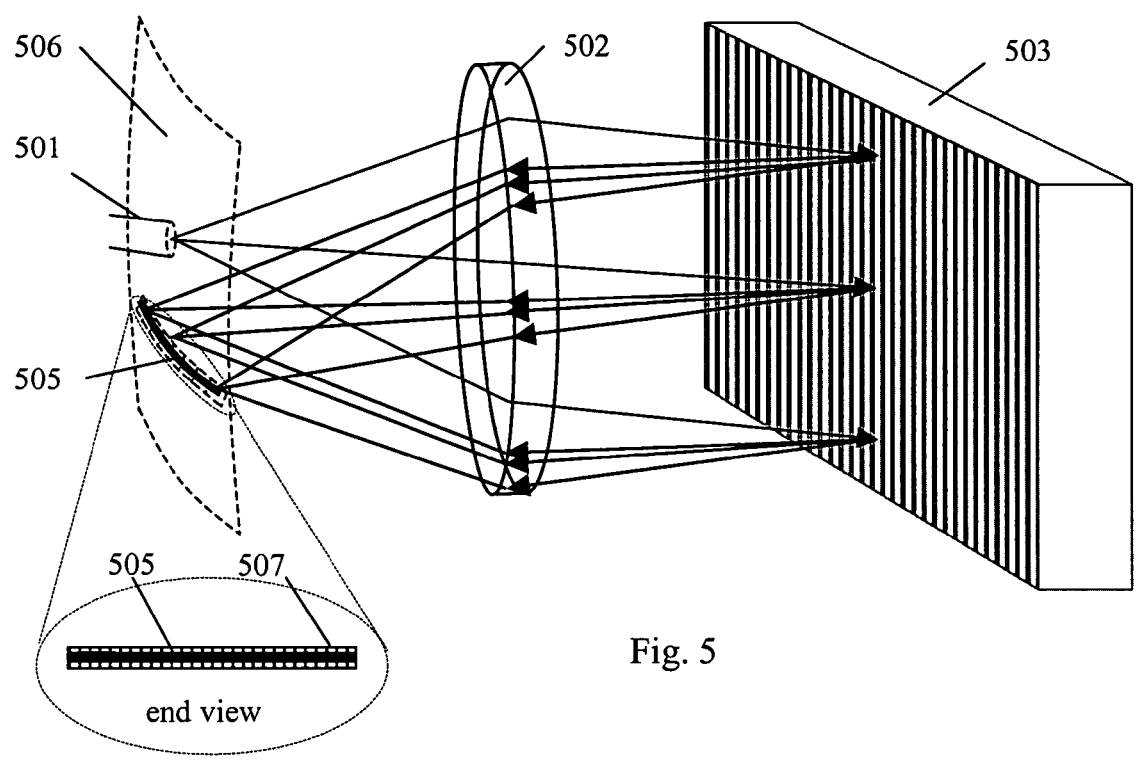
FIG. 5 shows a preferred embodiment of a Littrow conical diffraction configuration in which a lens with a negative distortion is placed in the optical path with a certain vertical off axis displacement so that the conically diffracted beams will suffer a negative distortion from the aberrant lens that substantially compensates the positive distortion of the diffracted beam.

FIG. 5 illustrates a preferred approach for compensating for the bending of the focused spectral line 305 caused by conical diffraction as shown in FIG. 3(a). More specifically, a common (generally thicker) aberrant lens 502 with a negative (barrel) distortion is preferably placed in the optical path of both the input and the output arms with a certain vertical off axis displacement for the output beams as shown in FIG. 5. The principal central ray of the input beam from the optical fiber 501 will pass the common lens 502 through the vertical central line of the lens and the principal central light rays of the conically diffracted beams from the grating 503 will pass through the common lens 502 from the lower half of the lens, thus suffering a negative distortion from the lens that substantially compensates the positive distortion of the conically diffracted beams. As a result, the imaged spectrally dispersed line 505 on the curved image surface 506 is substantially straightened laterally as can be seen from the inset end view of FIG. 5.

Note that the above paragraph should not be interpreted as limiting the invention to the use of the common lens in a Littrow spectrometer for compensating the distortion of conically diffracted light beams. The distortion of conically diffracted beams in a Littrow spectrometer can also be compensated in other ways. For example, the lens used for distortion compensation can be a separate lens only for the output arm of the spectrometer. However, a more compact arrangement can be achieved by sharing the lens in front of the grating. In addition, the spectrally dispersed beams do not need to be limited to the same diffraction order and can include overlapping diffraction orders, possibly with some crossed dispersion to separate the orders vertically. Furthermore, the present invention is not limited to the use of off-axis-image-induced-distortion compensation; other types of lenses can also be used as long as they can achieve a similar effect. For example, a lens with a positive distortion can also be used as long as the spectrally diffracted beams are arranged such that the principal central rays will pass the lens through the upper half of the lens, assuming that the grating is tipped toward the lens, or the lower half if the grating is tipped away. Alternatively, a specially designed lens can also be used in such a way that even if the principal central rays of the diffracted beams will pass the vertical central part of the lens, the lens will still introduce a compensating distortion to straighten the focused spectral line.

An issue that may be associated with the spectrometer as shown in FIG. 5 is that the well focused spectral line may still lie on a curved surface 506 (also seen as 306 in FIG. 3(b)) of positive curvature as is often the case for a conventional imaging system. The result of this curved surface 506 of good focus is that the spectral line cannot be well focused onto all the pixels of a planar detector array. Instead, the focused spot size on each pixel will vary across the sensor.

Figure 6A:
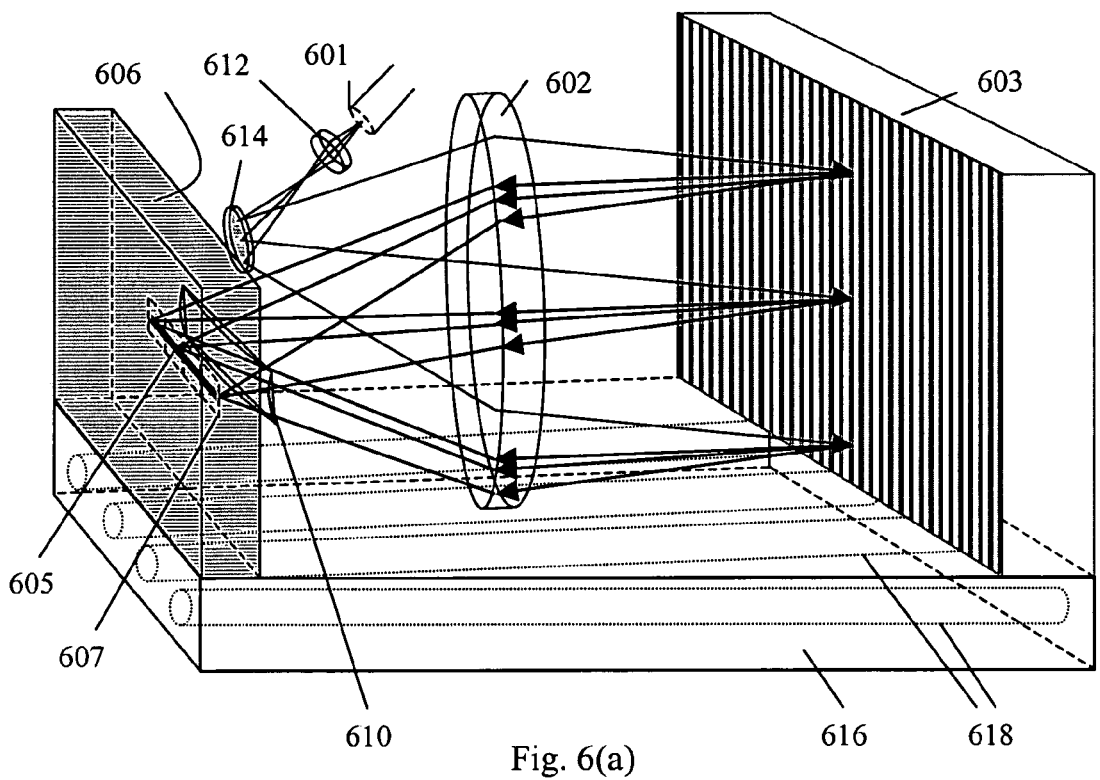
FIG. 6 (a) shows perspective view of a preferred embodiment of a conical diffraction based Littrow spectrometer in which a field flattening lens is used to further straighten the focused spectral line, an input port lens is used for numerical aperture matching and a deflecting mirror is arranged in the front of the detector array to further reduced the overall size of the spectrometer.
Figure 6B:
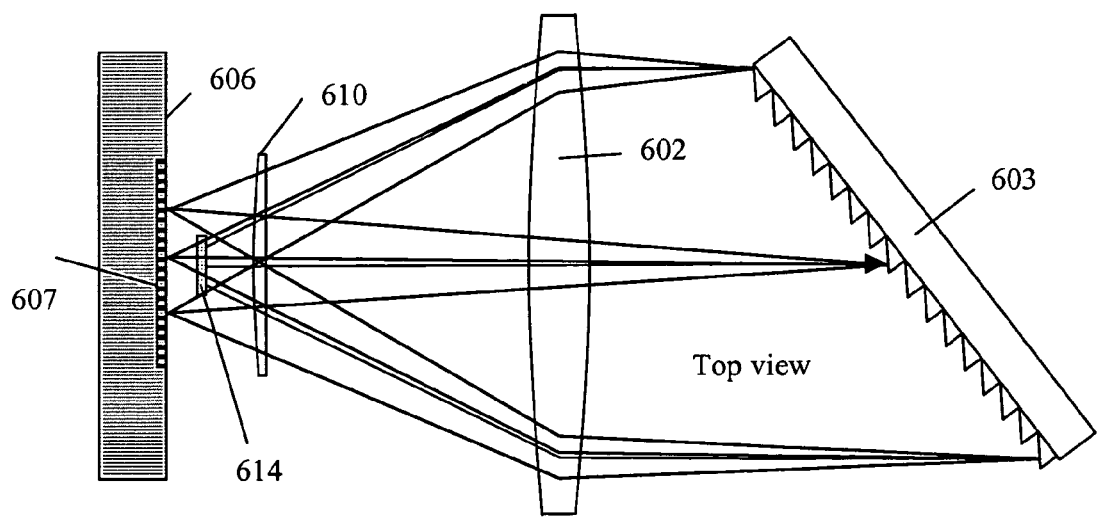

As a solution to this problem, according to one or more embodiments of the present invention, a field flattening lens 610 is inserted in the output arm in front of the linear detector array 607 to substantially flatten the surface of good focus so that the focal points of the spectral line 605 can be well aligned on the flat surface 606 of the detector array as shown in FIGS. 6 (*a*) and (*b*). It should be understood that the above-mentioned field flattening lens can be in any suitable form such as in the form of a meniscus lens. The field flattening effect can also be achieved through the design of the common lens, or the use of a combination of lenses. Thus, in a preferred embodiment, the invention provides an approach to substantially straighten the focused spectral line in a conical diffraction Littrow spectrometer wherein compensation is provided for either or both the distortion of the spectrally dispersed beam in the transverse direction (across the array as seen in FIG. 5) or in the direction of propagation of the beam (corrected by field flattening lens of FIG. 6). Such distortion compensation should be interpreted as a way to straighten the focused spectral line in a 3D space so that a planar photodetector array can be aligned with the straightened focused spectral line to enable a stable and true conversion of the optical energy as a function of wavelength into electrical signals.

Another issue that may be associated with the configuration of FIG. 5 is that when the input beam comes from a single mode optical fiber as is the case for most practical SD-OCT systems, the numerical aperture of the fiber may not match the numerical aperture of the spectrometer. As one additional feature of the present invention, an input lens 612 is inserted in the input arm near the fiber tip 601 to match the numerical aperture of the input arm to that of the output arm as is also shown in FIG. 6(*a*). It should be understood that there are other ways to change the numerical aperture of the light coming out of a single mode fiber tip, for example, the numerical aperture can be changed by shaping the fiber tip into a lens directly or attaching a grin lens to the fiber.

Still another issue of the configuration as shown in FIG. 5 is that the packaged size of commercially available line scan cameras are generally much larger than the photosensitive area of the pixel array. Hence it is not possible to put an optical fiber just above the pixel array from behind the camera body. As one preferred additional feature of the present invention, a light beam folding mirror 614 is mounted in the front of the line scan camera as shown in FIGS. 6 (*a*) and (*b*) so that the relative angle between the input arm and the output arm can be kept small, for example, less than about 10 degrees. This arrangement can scale down the degree of distortion introduced to the diffracted spectral line by conical diffraction since the diffraction now approaches the classical in-plane diffraction. The arrangement also substantially reduces the size of the whole spectrometer to make it more compact and also more stable.

In application to SD-OCT, relatively large static misalignments that move the spectrum along the line-scan pixel array can be tolerated. Such lateral misalignments shift the recorded spectral interference fringes, but do not change their spatial frequency, to first order in the shift. The frequency of the fringes changes only through the nonlinearity in the relation between optical frequency and position on the line-scan pixel array. The relation between the position, parameterized by a variable x running from −0.5 to +0.5 along the pixel array, and optical frequency ν can be approximated by a polynomial. As an example, for a Littrow configuration covering a range Δν of optical frequencies that is 10% of the central optical frequency, a typical approximate relation is $\nu=C[x+0.15x^2+0.05x^3]$ where C is a constant. Those skilled in the art of OCT can compute the impact on OCT image quality of an un-compensated shift δx of the spectrum relative to the camera. A shift of δx=0.05, ten pixels on a 2048-pixel camera, is often tolerable.

In another preferred embodiment of the present invention, the spectrometer is mounted on a base material that has a substantially low thermal expansion. While certain materials such as Invar have a thermal expansion coefficient close to zero and can be directly used as the base for the invented spectrometer, the base can also be made from a composite material having compensating coefficients of thermal expansion. For example, the composite material can be composed of two materials with one having a positive coefficient of thermal expansion and the other a negative coefficient of thermal expansion. As shown in FIG. 6(*a*), the base 616 can be a metal with a positive coefficient of thermal expansion and the embedded bars 618 can be a different material with a negative coefficient of thermal expansion. Due to the nearly coaxial feature of the diffracted beams with respect to the input beam in the Littrow spectrometer configuration, one can compensate for any thermally induced variation of the imaging function to the lenses by selecting an opposing thermal expansion coefficient of the base. For example, the focal length of glass lenses tends to change with temperature, which change can be compensated by thermal expansion or contraction of the base.

Figure 7:
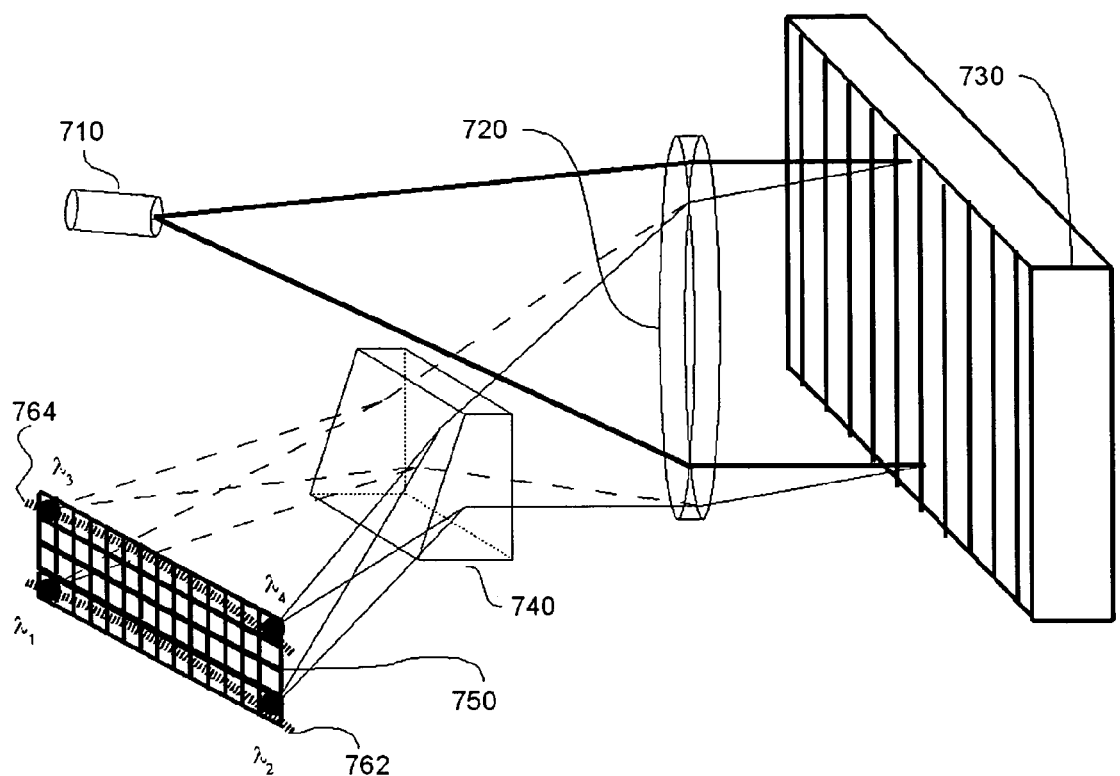
FIG. 7 (a) shows a preferred embodiment of the cross-dispersed echelle spectrograph in Littrow configuration using a prism as the low-dispersion element.
Figure 7:
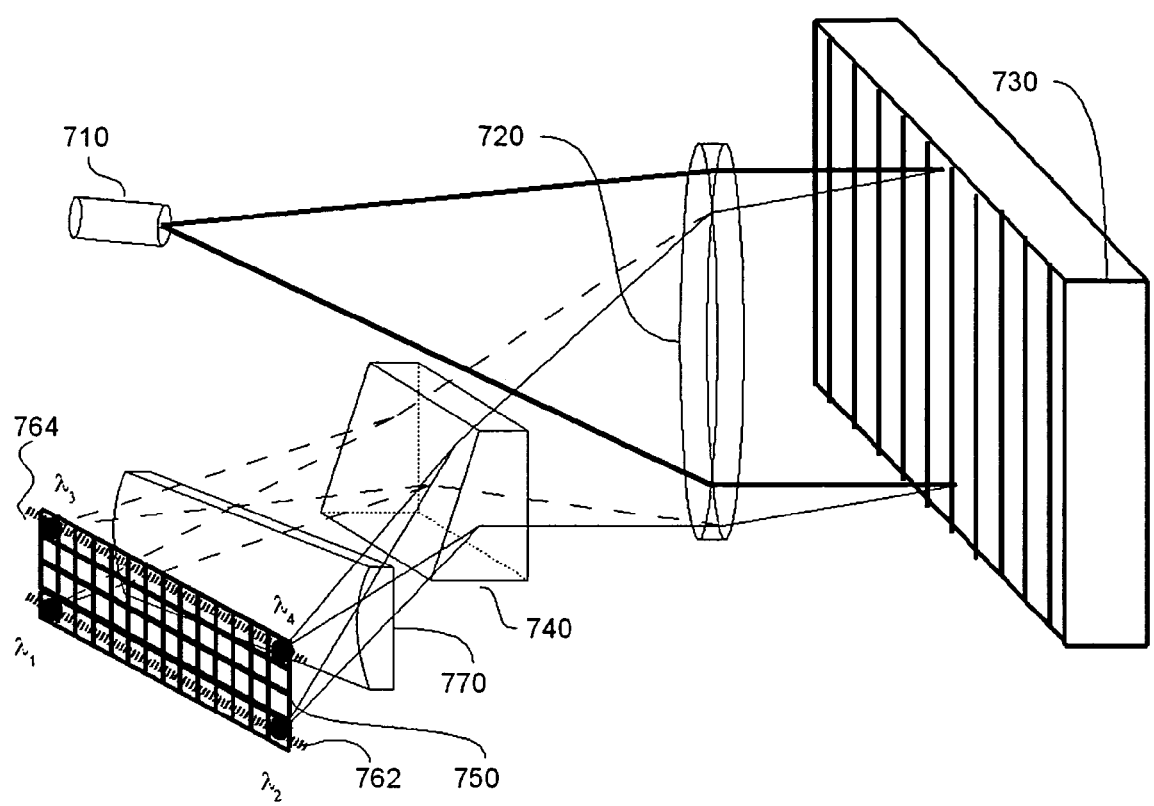

FIG. 7(*a*) illustrates a preferred approach for implementing a cross-dispersed echelle spectrograph in Littrow configuration. The interference signal coming from a preferably fiber-coupled light source 710 is traveling through lens system 720 before being dispersed at the echelle grating 730. In Littrow configuration, the dispersed light then travels through lens system 720 again, before being cross-dispersed at a low-dispersive element 740, in this case a prism, but it can as well be a grating. The overlapping diffraction orders of the echelle grating are then vertically displaced onto the two-dimensional array detector or stacked multi-line detector array 750. Two focused partial spectra 762 and 764 from two orders of diffraction are represented in FIG. 7(*a*); in general several orders of diffraction contain significant amounts of light and are collected by detector array 750.

The vertical displacement provided by element 740 depends on wavelength, which varies significantly across the partial spectra within each order of diffraction. Thus the vertical displacement varies across the wavelength range within each order, resulting in a slant of the focused partial spectra. The slant can be removed by slightly rotating the echelle grating with respect to the detector array, the rotation being about an axis normal to the echelle grating surface.

Each order of diffraction typically covers only a fraction of the full spectral range. The diffraction efficiency, as a function of angle, for grating 730, determines the horizontal extent over which each order contains significant diffracted light. The wavelength ranges detected in two consecutive orders, ranges $\lambda_1$ through $\lambda_2$ and $\lambda_3$ through $\lambda_4$, preferably overlap, $\lambda_1 < \lambda_3 < \lambda_2 < \lambda_4$, so that there are no gaps in the set of wavelengths detected. When the echelle grating is used in higher orders of diffraction, the separation in wavelength between consecutive orders ($\lambda_1 - \lambda_3$ for example) becomes smaller. At sufficiently high orders of diffraction, the separation between consecutive orders becomes less than the bandwidth of the broadband source, so partial spectra within the source bandwidth overlap after diffraction by the echelle, to be separated only by the cross dispersing element. The cross-dispersed spectrometer shows its distinct advantages when several orders of diffraction overlap; that is, when several overlapping wavelengths, such as $\lambda_1$, $\lambda_3$, etc., lie within the source bandwidth. An appropriate definition of bandwidth for this purpose is the full-width of the spectrum at 10% of the peak intensity.

FIG. 7(b) illustrates the preferred embodiment, including an additional field flattening lens 770 to bring the focal field, the surface on which the individual wavelengths come to a focus, closer to the flat plane of the detector array. The placement of field flattening lens 770 and common lens 720 are chosen to substantially cancel the distortion effect of conical diffraction, bringing the partial spectra to focus in nearly straight lines on the detector array.

Figure 7C:
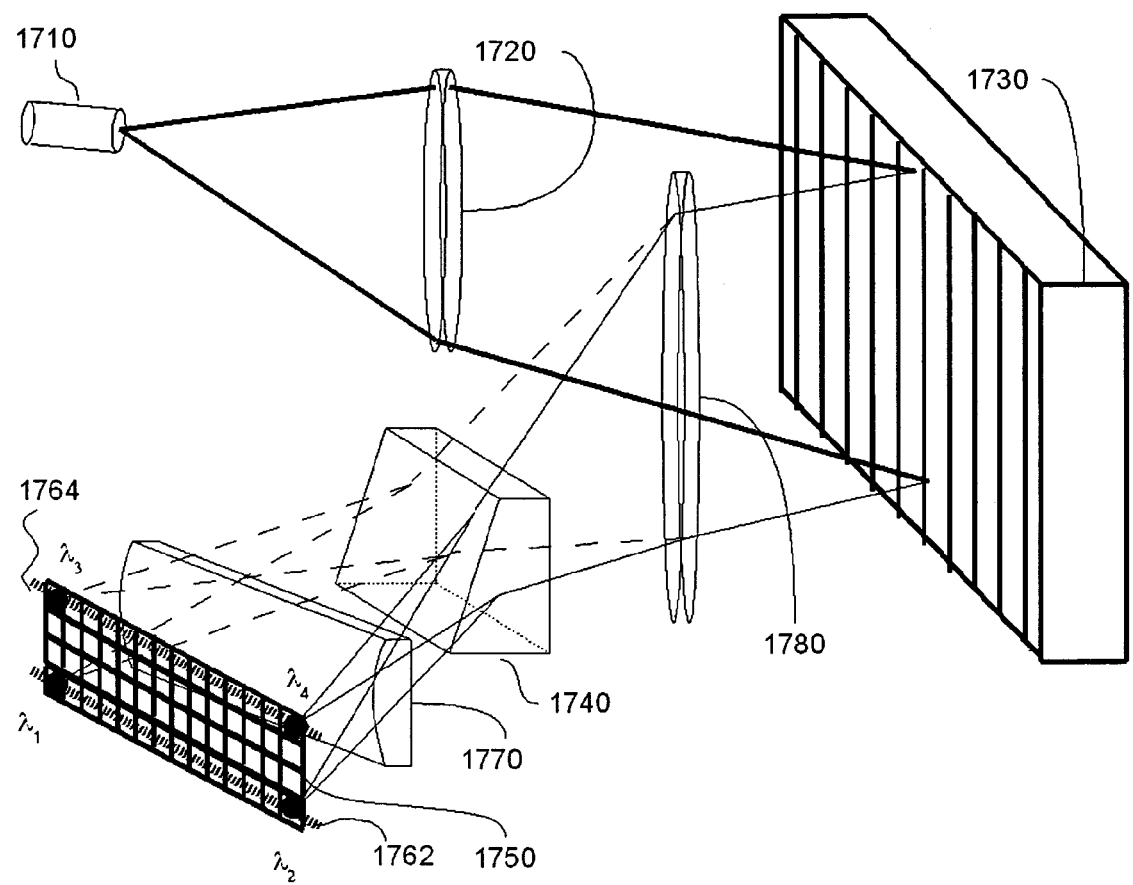

FIG. 7(c) illustrates an alternative embodiment, in which grating 1730 is used outside the Littrow configuration. Light from fiber tip 1710 is collimated by collimating lens 1720 and propagates towards a blazed echelle grating 1730. The diffracted beams pass through focusing lens 1780 which brings each wavelength to a focus near the plane of detector array 1750. Prism 1740 serves to separate the orders of diffraction in the vertical direction. Two focused partial spectra 1762 and 1764 from two orders of diffraction are represented in FIG. 7(c); in general several orders of diffraction are collected. Field flattening lens 1770 is designed to bring each wavelength to focus at a point close to the plane of detector array 1750.

The design calculations for application of this cross-dispersed spectrometer to SD-OCT are illustrated by an example. If the source spectrum is centered at 850 nm, SD-OCT with axial resolution of 5 microns requires collection of interference spectra over a bandwidth of approximately $\Delta\lambda=130$ nm. The longitudinal positions of scattering centers are encoded by the frequency of oscillation of interference fringes across the spectrum, with scatterers at greater longitudinal depth causing faster oscillation across the spectrum. The ability to image using SD-OCT over a large depth range therefore depends on the ability of the spectrometer to resolve fast oscillations across the spectrum. In order to image a depth range of 5 mm, we need to resolve fringes having period 0.07 nm. Dispersing the spectrum so that the wavelength changes 0.03 nm per pixel in the detector array provides a practical margin of over-sampling.

The Micron MT9M413 sensor is a detector array with 1280 pixels in each row, the pixels spaced at 12 μm. A dispersion of 0.03 nm per pixel on this sensor means that each 15.36-mm-long row covers 38 nm of the spectrum.

The diffraction efficiency of an echelle grating, as a function of diffraction angle, has a full-width at half maximum that covers a wavelength range equal to separation in wavelength between successive orders (Palmer, *Diffraction Grating Handbook* § 11.5). In order to collect the majority of the diffracted light, it is preferred to design the spectrometer so that the rows of the detector array are approximately twice as wide as the bright area of the partial spectra that is defined by the efficiency curve. (This choice corresponds to putting the detector array edges at the first zeros of the single-slit diffraction pattern from each groove.) In this case the wavelength separation between orders is half the spectral range collected on each row; the wavelength separation between orders should be 19 nm in this example. The wavelength separation between orders is $\lambda/m$, where m is one of the orders, so we need to choose the grating so that the orders are near m=840 nm/19 nm=44.

If a compact design is desired, it is preferable to operate close to the Littrow angles. In this case, the grating equation becomes nearly $m\lambda=2d\sin\theta$ where $\theta$ is the blaze angle. A common blaze angle of echelle gratings is 63.43° (arctangent of 2). For this blaze angle and the order chosen above, the groove density must be approximately 48 grooves/mm.

The closest match in the Richardson catalog (now Spectra Physics part number 53-size-415E) has 52.67 grooves/mm. The spread in diffraction angles that we want to collect, corresponding to $2\lambda/m=38$ nm spectral width, can be determined from the grating equation as ±5.6° relative to the blaze angle. To fit this spectral width onto one row of the camera, 15.36 mm long, we need an effective focal length of 70 mm.

Figure 8:
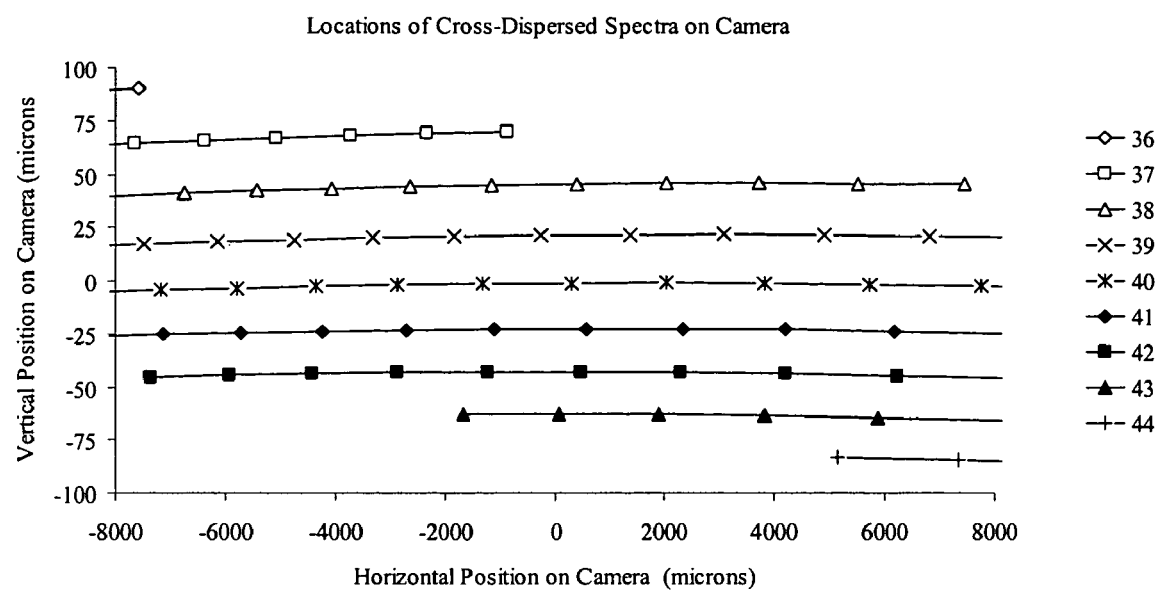
FIG. 8 shows the locations of the spectral orders on the camera under conditions described in the body of this patent.

One pass through a 17° prism made of SF11 glass (or two passes through 8°) will separate the orders by 24 μm on the camera, so consecutive orders of diffraction fall on every second row, given the 12-μm pixel size. (The dispersion of SF11 will not space the orders equally. The calculation generating the plot in FIG. 8 below models the prism approximately, assuming the angle of refraction is a linear function of wavelength.) Rotation of the echelle by 0.17° makes the orders roughly horizontal on the camera. The result, shown in FIG. 8, spreads our spectrum over 5 orders, m=38 to 42, with a small amount of light in orders 37 and 43. The curves run from 785 nm to 915 nm with a marker every 5 nm. The wavelength ranges falling on the sensor in each of the diffraction orders are:

m=42: 787 nm-828 nm,
m=41: 805 nm-847 nm,
m=40: 826 nm-868 nm,
m=39: 847 nm-891 nm, and
m=38: 869 nm-913 nm.

With good alignment, we could read out the spectrum in 6400 pixels. The grating diffracts most light within angles within a 5.6° spread centered on the blaze angle; this set of angles being imaged onto the central 7000 microns horizontally on the camera.

In summary, the predicted axial resolution and depth range are both approximately equivalent to what one can achieve using a 4096-pixel linear array, but the largest camera dimension is 15 mm in the cross-dispersed spectrometer instead of 41 mm in the linear spectrometer. The analog-to-digital conversion and readout electronics provided with the MT9M413 sensor can output this 6400-pixel spectrum at 100 k spectra per second. The design accommodates additional fiber inputs, producing additional spectra above or below the existing spectra. One use of additional inputs is to simultaneously record several phases of interference. The interspersed sampling of the cross-dispersed spectrometer reduces artifacts due to aliasing, because the average sampling density, with 5 rows of 1280 pixels giving us 6400 sample points on the spectrum, is greater than the sampling density provided by the 4096 pixels of the comparable linear spectrometer.

In a second set of example design calculations, we suppose there is a 128×64 pixel sensor. If the pixels in a row are spaced at 12 μm, then to get our desired dispersion we should put 3.8 nm of the spectrum on each 1.536-mm-long row. The separation between orders, $\lambda/m$, would 1.9 nm so we need to operate in orders near m=440. The grating equation, with left hand side $m\lambda=440\times0.84$ μm=370 μm, forces a large spacing d; such gratings are typically constructed by stacked plates and called echelons. We have not identified a source for an echelon, but postulate a step spacing of d=200 μm and a step width of 40 μm so that the effective blaze angle is arctangent(5)=78.7°. The angular spread, corresponding again to twice the wavelength separation between orders, is ±1.23°. To fit this spectral width onto one row of the camera, 1.536 mm long, we need an effective focal length of 35 mm. With consecutive orders so close in wavelength, the cross-dispersing element must have greater dispersion that a prism. If we choose to put spectra on consecutive rows, 12 µm apart, dispersion of approximately 0.010°/nm is required. A first-order grating with 150 grooves per millimeter would suffice as the cross-dispersing element.

SD-OCT is described by Leitgeb et al., ("Ultrahigh resolution Fourier domain optical coherence tomography", *Optics Express* 12 10, pp. 2156-2165 (2004)), by Choma and Sarunic ("Sensitivity advantage of swept source and Fourier domain optical coherence tomography." *Optics Express* 11(18): 2183-2189 (2003)), and by de Boer et al. ("Improved signal-to-noise ratio in spectral-domain compared with time-domain optical coherence tomography." *Optics Letters* 28(21): 2067-2069 (2003)). As we have mentioned in the background section, so far, all prior art SD-OCT systems have used two lenses in the spectrometer in which one lens is used for collimating the input beam to propagate towards the grating and the other is used to focus the dispersed spectral beams onto a detector array. A novel feature of the present invention is the incorporation of a spectrometer in an SD-OCT system that uses one or more common shared focusing element(s) for both the input as well as the dispersed output beams.

Figure 9:
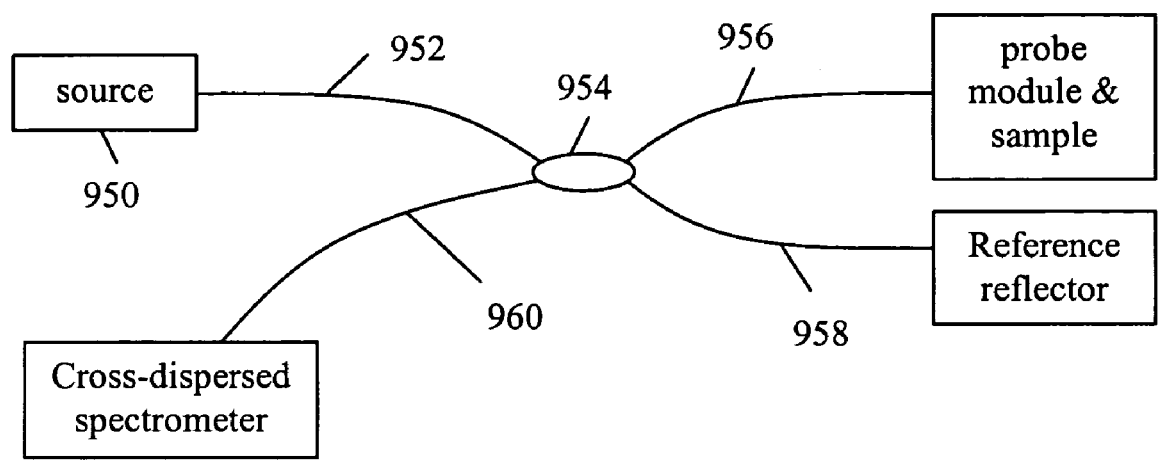
FIG. 9 shows the use of a cross-dispersed spectrometer in a SD-OCT system.

FIG. 9 shows the preferred embodiment of a cross-dispersed spectrometer (as shown in FIG. 7) as used in a spectral domain optical coherence tomography (SD-OCT) system. In this preferred embodiment, light from a broadband source 950 is directed through a single mode fiber 952 to a fiber coupler 954 and is split into the sample arm 956 and the reference arm 958. Light returned from the sample arm 956 interferes with light returned from the reference arm 958. Part of the interfered optical beam is guided by the detection arm 960 and sent to the cross-dispersed spectrometer. The cross-dispersed spectrometer is preferably one that has one or more of the presently invented advantageous features as discussed before.

The Fourier transform of the spectral intensities recorded by detector array 750 provides the reflectance distribution along the path of the sample, e.g. along the depth within the sample. The detected reflectance distribution includes not only specular reflections, but also other scattering processes that return light to the spectrometer. Details of the processing steps required to form a high resolution image of the reflectance are known in the art and described by Leitgeb et al., ("Ultrahigh resolution Fourier domain optical coherence tomograph", *Optics Express* 12 10, pp. 2156-2165 (2004)), by Choma and Sarunic ("Sensitivity advantage of swept source and Fourier domain optical coherence tomography." *Optics Express* 11(18): 2183-2189 (2003)), and by deBoer et al. ("Improved signal-to-noise ratio in spectral-domain compared with time-domain optical coherence tomography." *Optics Letters* 28(21): 2067-2069 (2003)).

Note that there may be a large number of variations of the optical interferometer as well as of the cross-dispersed spectrometer in the SD-OCT system. For example, the optical interferometer does not need to be limited to the Michelson type and can be Mach-Zehnder or a combination of Michelson and Mach-Zehnder or others as long as it can split an input beam into at least two beams and recombine some portion of the split beams. The reference arm hence does not need to be restricted to reflective type and can be transmissive (for example, the reference arm can include a loop back to the beam splitter 954). The optical path does not need to be restricted to optical fibers and can be bulk optics based or a combination of fiber optics and bulk optics. Other optical component can be included in the optical path to manipulate the property of the light beam, examples include polarizer(s), polarization controller(s), polarization beam splitter(s), waveplate(s), lens(es), mirror(s), non-polarization beam splitter(s), and so on, in the fiber optics or bulk optics form. Other configurations that have been used for OCT systems include balanced detection scheme (see for example, US20040239938/WO04111929) and high optical power efficiency designs (see for example, U.S. Pat. No. 6,657,727). These can all be combined with the presently invented spectrometer for SD-OCT applications.

The spectrometer in the spectral domain OCT system does not need to be limited to a conical diffraction Littrow spectrometer. It can be a classical in-plane diffraction spectrometer. In addition, the first grating, the one that is an echelle in the preferred embodiment, does not need to be restricted to a plane grating. This first grating can be a curved or a concave grating that can serve both the dispersing and the focusing functions. A main feature of the present invention is the use of a spectrometer in an SD-OCT system wherein the spectrometer has one or more shared focusing element(s) for the input and diffracted output beams. The shared focusing element(s) can be a lens or a combination of lenses, or a curved/concave grating or a curved/concave mirror.

Figure 10:
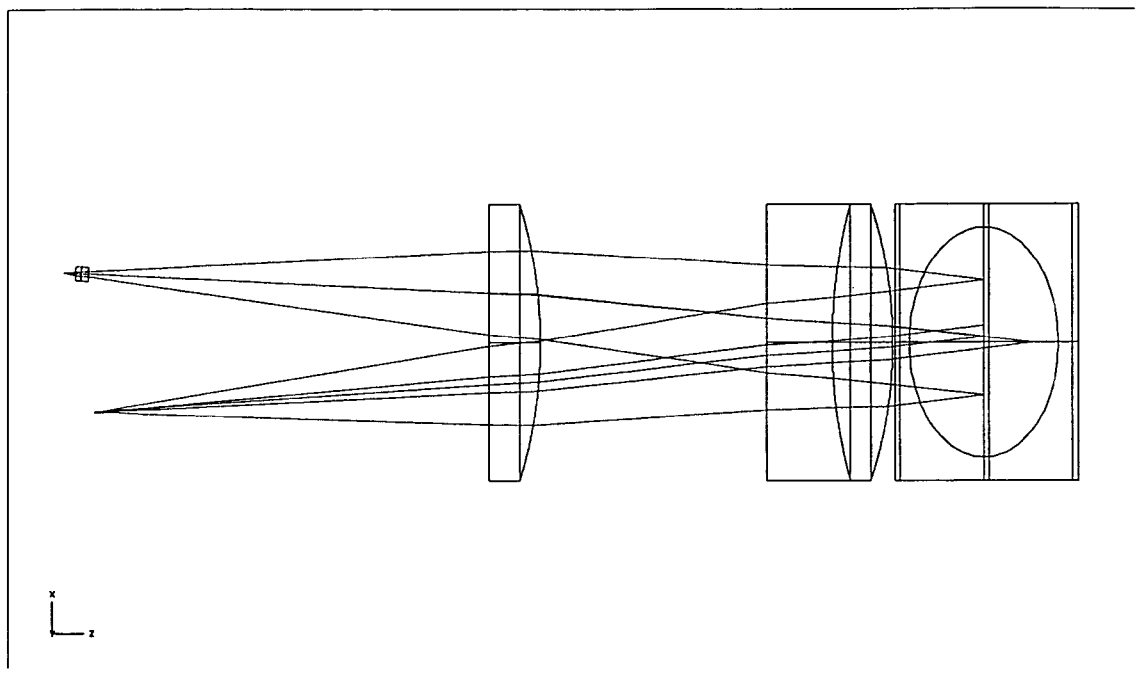
FIG. 10 (a) shows the design of a lens system for a Littrow spectrometer in a SD-OCT system, consisting of a doublet and a singlet, which collectively act as the shared common lens for the input beam and the diffracted output beams.
Figure 10:
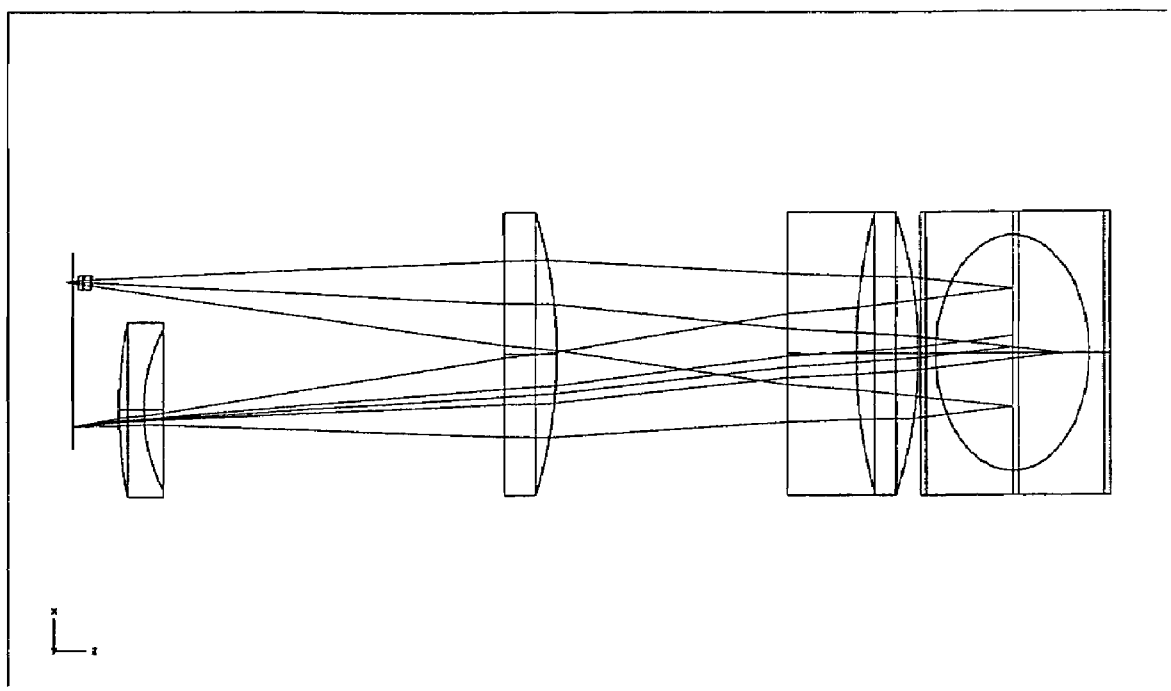

In a preferred embodiment, the spectrometer in the spectral domain OCT system is a conical diffraction Littrow spectrometer with the presently invented advantageous features. FIGS. 10 (*a*) and (*b*) show a preferred embodiment of a lens design within the spectrometer that can compensate for the distortion introduced by conical diffraction. FIG. 10 (*a*) shows the design of a lens system for a Littrow spectrometer in an SD-OCT system, consisting of a doublet 1002 and a singlet 1004, which collectively act as the shared common lens for the input beam and the diffracted output beams. The doublet 1002 is a combination of two lenses made of crown and flint glasses. The designed lens system has an effective focal length of 130 mm. The computer models a broadband light beam with a center wavelength of about 840 nm and a spectral width from 795 nm to 885 nm sent to a 1500 groove/mm grating that is tipped with a tip angle of about 5 degrees to enable conical diffraction and the diffracted beams are focused onto a 30 mm wide pixel array of a line scan or CCD camera. The set of lenses in the model depicted in FIG. 10(*a*) have negative (barrel) distortion that causes the focused spectral line to curve up, opposite the situation shown in inset portion of FIG. 3*a*, with the ends of the spectrum now 15 microns above the center. FIG. 10 (*b*) shows that with the insertion and appropriate placement of a field flattening lens 1006 that has an approximately 3.1% positive (pincushion) distortion at the ends of the CCD sensor, the focused spectral line can be straightened to have only a maximum of 1 micron deviation from a straight line.

Alternatively, a common lens can be shared in front of the grating by both the input and output arms and in addition, the shared lens can have a certain distortion that substantially compensates for the distortion introduced to the diffracted spectral beams by conical diffraction. Additional optical components can be placed in either the input or output or both arms to provide additional functions. For example, a field flattening lens can be placed in the output arm to further straighten the focused spectral lines. A beam folding mirror can be arranged in the input arm to enable the acceptance of the input light beam from the front side of the camera. An input lens can also be used to function for numerical aperture matching. For SD-OCT applications, a high data rate of the detector array (preferably greater than 1000 lines per second) is preferably desired.

Another issue not fully addressed by previous SD-OCT designs is the polarization dependence of the spectrometer.

A standard grating is generally more efficient for one polarization state than for the orthogonal polarization state. As can be seen from a US patent applications (US20040239943, US20050213103), one approach to solve the problem is to select only one polarization direction of the interfered beam and to launch the linearly polarized beam into the spectrometer with a selected orientation. Another approach is to separate the interfered beam into two perpendicular polarizations such that two linearly polarized interfered beams can be sent to two spectrometers. The former approach may result in a reduced signal to noise ratio and the latter approach requires two spectrometers which will substantially increase the cost of the system.

The input to the spectrometer in an SD-OCT will typically have varying polarization state, unless measures are taken to control the polarization. In OCT it is advantageous to ensure a high value of the modulation depth of the interfered beam by adjusting the polarization state of either the reference arm or the sample arm or both arms in the interferometer so that the polarizations of the two beams are substantially matched. This adjustment is commonly done individually for each sample to be measured, so as to compensate for rotation of the polarization in the sample, and for rotation of polarization in the optics leading to the sample, possibly including optical fiber. One could also adjust the polarization state of the interfered beam in the detection arm of the interferometer so that the final state of polarization of the interfered beam shining onto the grating in the spectrometer is substantially the polarization state for which the grating has higher diffraction efficiency. However, in fiber interferometers commonly used for OCT, the final polarization state depends upon the bending of the optical fiber in any arm of the interferometer, which may change as a function of temperature and mechanical vibration, so it may be necessary to employ dynamic controlling of the polarization state in a fiber. This obviously will add cost to an SD-OCT system.

If the spectrometer is substantially polarization-independent, then the SD-OCT system need only substantially match the polarization states between sample and reference arms, sending the interfered beam to the spectrometer with no further polarization control. A substantially polarization-independent spectrometer is advantageous in the design of a simple and reliable SD-OCT system.

As one aspect of the invention, the cross-dispersed spectrometer in an SD-OCT system is made substantially polarization independent. A first simple way is to select a proper blaze angle and a proper grating groove density such that the diffraction efficiency for the mutually orthogonal S and P polarization cross with each other, i.e. is substantially equal, for the central wavelength of interest. A second simple way to compensate for the polarization dependence is to insert a polarization compensating optical element along detection arm 960 or within the cross-dispersed spectrometer anywhere along the optical path between the entry and the detector array. Such a polarization compensator can be a partial polarizer so that while light in one polarization direction is substantially transmitted, light in the orthogonal polarization direction is partially absorbed or reflected away from the spectrometer. There may be many partial polarizers and a good example is a single piece or a stacked multiple pieces of glass tilted around the Brewster angle.

Figure 11:
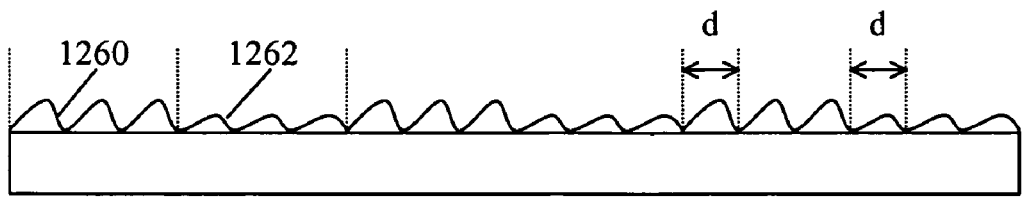
FIG. 11 (a) shows a grating with a surface relief profile that has two different grating elements of the same grating period but different modulation depth or blaze angles to render the grating substantially polarization independent.
Figure 11:
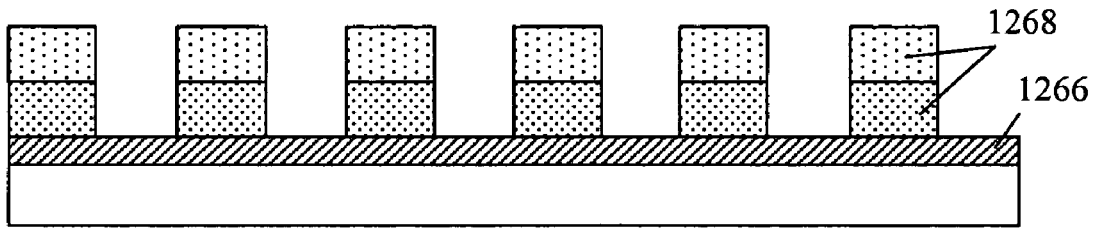
Figure 11:
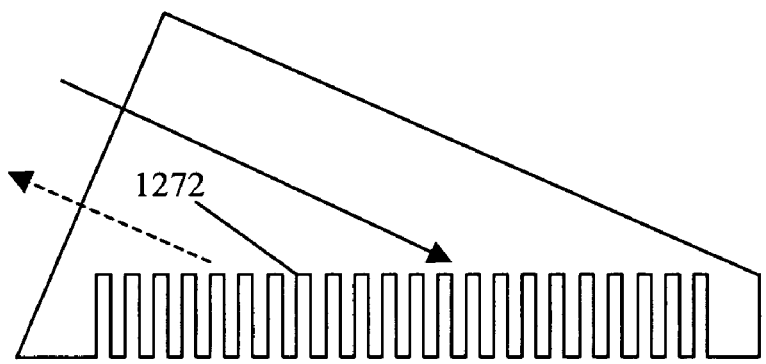
Figure 11:
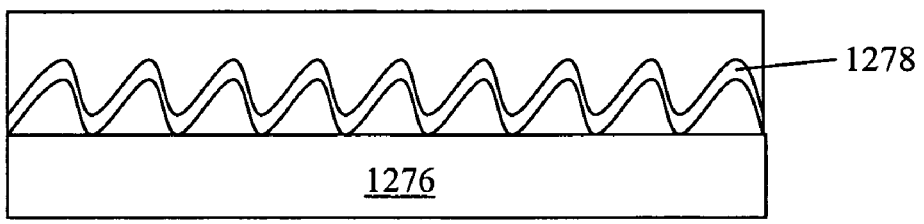
Figure 11:
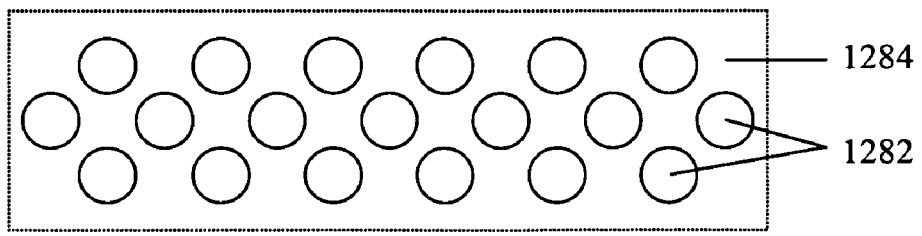

Alternatively, the echelle grating in the spectrometer can be made substantially polarization independent in various ways as shown in FIG. 11 (*a*) to (*e*). A first example is a grating with a surface relief profile that has two different grating elements 1260 and 1262 of the same grating period but different modulation depth or blaze angles to render the grating substantially polarization independent (see for example, U.S. Pat. No. 6,487,019) as shown in FIG. 11 (*a*). Note that the number of repeating surface relief profiles in each grating element 1260 or 1262 can vary from 1 to N, where N is an integer. A second example is a hybrid metallic-dielectric grating that has a metallic base layer 1266 and layers of dielectric materials of varying refractive index 1268 to render the grating substantially polarization independent (see for example, U.S. Pat. No. 6,754,006) as shown in FIG. 11 (*b*). A third example is a lamellar volume grating that has an approximately rectangular grating profile 1272 with a height-to-width ratio of the grooves greater than two to render the grating substantially polarization independent (see for example, U.S. Pat. No. 6,724,533) as shown in FIG. 11 (*c*). A fourth example is a grating with a substrate 1276 and a reflective material 1278 adjacent the substrate 1276 to render the grating substantially polarization independent (see for example, U.S. Pat. No. 6,577,786) as shown in FIG. 11 (*d*). Another example is a blazed photonic crystal grating made with embedded circular rods 1282 in another optical medium 1284 that has a high diffraction efficiency and a high degree of polarization independence (see for example, Popov E. et al. "Almost perfect blazing by photonic crystal rod gratings", Applied Optics 40(15) 2417-2422) as shown in FIG. 12 (*d*).

It should be understood that the presently invented apparatus(es) can also be extended to the associated methods. For example, one aspect of the invention is a method of performing spectral domain optical coherence tomography, comprising the steps of sending the interfered beam from an interferometer to a cross-dispersed spectrometer spectrometer for measurement of the spectral interferogram. Another aspect of the invention is a method of focusing conically diffracted spectra from several orders of diffractions substantially into straight lines, comprising the step of compensating the distortion induced by conical diffraction with a balancing distortion caused by the focusing optics. Still another aspect of the invention is a method of performing spectral domain optical coherence tomography, comprising the steps of sending the interfered beam from an interferometer to a polarization independent cross-dispersed spectrometer for measurement of the spectral interferogram.

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The following patents, patent applications and other documents are hereby incorporated by reference.

U.S. PATENT DOCUMENTS

U.S. Pat. No. 5,565,986
U.S. Pat. No. 6,487,019
U.S. Pat. No. 6,577,786
U.S. Pat. No. 6,657,727
U.S. Pat. No. 6,710,330
U.S. Pat. No. 6,724,533
U.S. Pat. No. 6,754,006
U.S. Pat. No. 6,757,113

U.S. Pat. No. 6,847,454
U.S. Pat. No. 6,859,317
US20040239938
US20040239943
US20050018201
US20050213103
U.S. patent application Ser. No. 11/196,043

FOREIGN PATENT DOCUMENTS

JP2000-046729
JP2001-174404
WO03062802
WO03073041
WO2004043245
WO2004111929

OTHER PUBLICATIONS

De-Boer, J. F., et al. (2003). "Improved signal-to-noise ratio in spectral-domain compared with time-domain optical coherence tomography." *Optics Letters* 28(21): 2067-2069

Choma, M. A., M. V. Sarunic, et al. (2003). "Sensitivity advantage of swept source and Fourier domain optical coherence tomography." *Optics Express* 11(18): 2183-2189

Leitgeb, R. A., et al. (2003). "Phase-shifting algorithm to achieve high-speed long-depth-range probing by frequency-domain optical coherence tomography." *Optics Letters* 28(22): 2201-2203

Leitgeb, R. A., et al. (2003). "Performance of Fourier domain vs. time domain optical coherence tomography." *Optics Express* 11(8): 889-894

Maystre D. et al. (1985) "Geometrical invariance property of gratings" *Applied Optics* 24(2): 215-216

McLean et al., 1998, "Design and development of NIR-SPEC: a near-infrared echelle spectrograph for the Keck II telescope", SPIE Proceedings Vol. 3354, pp 566

Popov E. et al. "Almost perfect blazing by photonic crystal rod gratings", *Applied Optics* 40(15): 2417-2422

Smith, L. M. and C. C. Dobson (1989). "Absolute displacement measurements using modulation of the spectrum of white light in a Michelson interferometer." *Applied Optics* 28(15): 3339-3342

Ko, T. H., J. G. Fujimoto, et al. (2005). "Comparison of Ultrahigh- and Standard-Resolution Optical Coherence Tomography for Imaging Macular Pathology." *Ophthalmology* 112(11): 1922-1935

Wojtkowski, M., et al. (2003). "Real-time in vivo imaging by high-speed spectral optical coherence tomography." *Optics Letters* 28(19): 1745-1747

Zeylikovich, I. et al. (1998). "Nonmechanical grating-generated scanning coherence microscopy." *Optics Letters* 23(23): 1797-1799

Palmer, C. (2002). *Diffraction Grating Handbook*, 5th edition. Richardson Grating Laboratory, (Rochester, N.Y.)

We claim:

1. A spectral domain optical coherence tomography (OCT) system for creating images of tissue structure in situ and in real time comprising:
   a broadband light source;
   a beam splitter for dividing the light along a sample and a reference path;
   a spectrometer for receiving light returned from both the sample and the reference paths, said spectrometer including a grating for angularly dispersing the light as a function of wavelength along a first axis and wherein at least two diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including at least two linear detector arrays, said arrays extending along said first axis, with one of said arrays being positioned to receive one of said diffraction orders and the other array being positioned to receive the other diffraction order, each array for generating output signals as a function of wavelength and wherein the output signals from the arrays are generated at a speed sufficient to allow the creation of images of tissue structure in situ and in real time; and
   a processor for analyzing the output signals to derive a reflectance distribution along the sample path.

2. An OCT system as recited in claim 1, wherein said optical element is a prism.

3. An OCT system as recited in claim 1, wherein said optical element is a grating.

4. An OCT system as recited in claim 1, wherein the grating and the detector array are positioned in a substantially Littrow condition.

5. An OCT system as recited in claim 1, wherein a common focusing optic is located in the path of both the received light and the dispersed light.

6. An OCT system as recited in claim 1, wherein the grating is tipped with respect to the received light to induce conical diffraction to thereby spatially separate the path of the dispersed light from the incident light along said second axis.

7. An OCT system as recited in claim 6, further including a means for reducing any non-linearities in the image of the beam related to the conical diffraction.

8. An OCT system as recited in claim 6, wherein the conical diffraction produces non-linearities in the footprint of the dispersed light with respect to the first axis and further including an optical element located between the grating and the array for reducing the non-linearity caused by the conical diffraction so the registration of the footprint with the array is improved.

9. An OCT system as recited in claim 1, wherein said beam splitter which divides the light along the sample and reference paths also functions to combine the light returned from both the sample and the reference paths.

10. An OCT system recited in claim 1, wherein the spectrometer is configured so that the output signals generated by the photodetector are substantially insensitive to the polarization state of the incoming light.

11. A spectral domain optical coherence tomography (OCT) system for creating images of tissue structure in situ and in real time comprising:
   a broadband light source;
   a beam splitter for dividing the light along a sample and a reference path;
   a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength and wherein the output signals from the arrays are generated at a speed sufficient to allow the creation of images of tissue structure in situ and in real time; and a processor for analyzing the output signals to derive a reflectance distribution along the sample path.

12. An OCT system as recited in claim 11, wherein said optical element is a prism.

13. An OCT system as recited in claim 11, wherein said optical element is a grating.

14. An OCT system as recited in claim 11, wherein the grating and the detector array are positioned in a substantially Littrow condition.

15. An OCT system as recited in claim 11, wherein a common focusing optic is located in the path of both the received light and the dispersed light.

16. An OCT system as recited in claim 11, wherein the grating is tipped with respect to the received light to induce conical diffraction to thereby spatially separate the path of the dispersed light from the incident light along said second axis.

17. An OCT system as recited in claim 16, further including a means for reducing any non-linearities in the image of the beam related to the conical diffraction.

18. An OCT system as recited in claim 16, wherein the conical diffraction produces non-linearities in the footprint of the dispersed light with respect to the first axis and further including an optical element located between the grating and the array for reducing the non-linearity caused by the conical diffraction so the registration of the footprint with the array is improved.

19. An OCT system as recited in claim 11, wherein said beam splitter which divides the light along the sample and reference paths also functions to combine the light returned from both the sample and the reference paths.

20. An OCT system recited in claim 11, wherein the spectrometer is configured so that the output signals generated by the photodetector are substantially insensitive to the polarization state of the incoming light.

21. A spectral domain optical coherence tomography (OCT) system for creating images of tissue structure in situ and in real time comprising:
a broadband light source;
a beam splitter for dividing the light along a sample and a reference path;
a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength, and wherein the grating and the detector array are positioned in a substantially Littrow condition, wherein the grating is tipped with respect to the received light to induce conical diffraction to thereby spatially separate the path of the dispersed light from the incident light along said second axis and wherein the output signals from the array are generated at a speed sufficient to allow the creation of images of tissue structure in situ and in real time; and
a processor for analyzing the output signals to derive a reflectance distribution along the sample path.

22. An OCT system as recited in claim 21, further including a means for reducing any non-linearities in the image of the beam related to the conical diffraction.

23. An OCT system as recited in claim 21, wherein the conical diffraction produces non-linearities in the footprint of the dispersed light with respect to the first axis and further including an optical element located between the grating and the array for reducing the non-linearity caused by the conical diffraction so the registration of the footprint with the array is improved.

24. An OCT system recited in claim 21, wherein the spectrometer is configured so that the output signals generated by the photodetector are substantially insensitive to the polarization state of the incoming light.

25. A spectral domain optical coherence tomography (OCT) system comprising:
a broadband light source;
a beam splitter for dividing the light along a sample and a reference path;
a spectrometer for receiving light returned from both the sample and the reference paths, said spectrometer including a grating for angularly dispersing the light as a function of wavelength along a first axis and wherein at least two diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including at least two linear detector arrays, said arrays extending along said first axis, with one of said arrays being positioned to receive one of said diffraction orders and the other array being positioned to receive the other diffraction order, each array for generating output signals as a function of wavelength and wherein a common focusing optic is located in the path of both the received light and the dispersed light; and
a processor for analyzing the output signals to derive a reflectance distribution along the sample path.

26. A spectral domain optical coherence tomography (OCT) system comprising:
a broadband light source;
a beam splitter for dividing the light along a sample and a reference path;
a spectrometer for receiving light returned from both the sample and the reference paths, said spectrometer including a grating for angularly dispersing the light as a function of wavelength along a first axis and wherein at least two diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including at least two linear detector arrays, said arrays extending along said first axis, with one of said arrays being positioned to receive one of said diffraction orders and the other array being positioned to receive the other diffraction order, each array for generating output signals as a function of wavelength, said spectrometer further including a means for reducing any non-linearities in the image of the beam related to the conical diffraction; and a processor for analyzing the output signals to derive a reflectance distribution along the sample path.

27. An OCT system as recited in claim 26, wherein the conical diffraction produces non-linearities in the footprint of the dispersed light with respect to the first axis and further including an optical element located between the grating and the array for reducing the non-linearity caused by the conical diffraction so the registration of the footprint with the array is improved.

28. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength along a first axis and wherein at least two diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including at least two linear detector arrays, said arrays extending along said first axis, with one of said arrays being positioned to receive one of said diffraction orders and the other array being positioned to receive the other diffraction order, each array for generating output signals as a function of wavelength and wherein the spectrometer is configured so that the output signals generated by the photodetector are substantially insensitive to the polarization state of the incoming light; and a processor for analyzing the output signals to derive a reflectance distribution along the sample path.

29. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength and wherein a common focusing optic is located in the path of both the received light and the dispersed light; and a processor for analyzing the output signals to derive a reflectance distribution along the sample path.

30. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength, said spectrometer further including a means for reducing any non-linearities in the image of the beam related to the conical diffraction; and a processor for analyzing the output signals to derive a reflectance distribution along the sample path.

31. An OCT system as recited in claim 30, wherein the conical diffraction produces non-linearities in the footprint of the dispersed light with respect to the first axis and further including an optical element located between the grating and the array for reducing the non-linearity caused by the conical diffraction so the registration of the footprint with the array is improved.

32. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength and wherein the spectrometer is configured so that the output signals generated by the photodetector are substantially insensitive to the polarization state of the incoming light; and a processor for analyzing the output signals to derive a reflectance distribution along the sample path.

33. A spectral domain optical coherence tomography (OCT) system comprising:

a broadband light source;

a beam splitter for dividing the light along a sample and a reference path;

a spectrometer for receiving light returned from both the sample and the reference paths, said spectrometer including a grating for angularly dispersing the light as a function of wavelength along a first axis and wherein a plurality of diffraction orders corresponding to different wavelength regions within the spectrum of the broadband light source spatially overlap along said first axis, said spectrometer further including an optical element for separating the diffraction orders along an axis perpendicular to the first axis, said spectrometer further including a photodetector including a two dimensional array of detector elements, with selected rows in said array detecting a range of wavelengths corresponding to selected ones of said diffraction orders, said photodetector for generating output signals as a function of wavelength, and wherein the grating and the detector array are positioned in a substantially Littrow condition, wherein the grating is tipped with respect to the received light to induce conical diffraction to thereby spatially separate the path of the dispersed light from the incident light along said second axis, further including a means for reducing any non-linearities in the image of the beam related to the conical diffraction; and a processor for analyzing the output signals to derive a reflectance distribution along the sample path.

* * * * *